(12) United States Patent
Bates et al.

(10) Patent No.: US 6,960,189 B2
(45) Date of Patent: Nov. 1, 2005

(54) PROXIMAL CATHETER ASSEMBLY ALLOWING FOR NATURAL AND SUCTION-ASSISTED ASPIRATION

(75) Inventors: Mark C. Bates, Charleston, WV (US); Michael Hogendijk, Palo Alto, CA (US)

(73) Assignee: Gore Enterprise Holdings, Newark, DE (US)

(*) Notice: Subject to any disclaimer, the term of this patent is extended or adjusted under 35 U.S.C. 154(b) by 443 days.

(21) Appl. No.: 10/112,807

(22) Filed: Mar. 29, 2002

(65) Prior Publication Data

US 2003/0187390 A1    Oct. 2, 2003

(51) Int. Cl.[7] .......................... A61M 1/00; A61M 5/00
(52) U.S. Cl. ...................... 604/119; 604/246; 604/35
(58) Field of Search .................. 604/35, 118, 119, 604/121, 246, 247–250

(56) References Cited

U.S. PATENT DOCUMENTS

| | | | |
|---|---|---|---|
| 4,230,128 A | 10/1980 | Aramayo | |
| 4,310,017 A | 1/1982 | Raines | |
| 4,397,335 A | 8/1983 | Doblar et al. | |
| 4,595,005 A | 6/1986 | Jinotti | |
| 4,642,097 A | 2/1987 | Siposs | |
| 4,668,215 A | 5/1987 | Allgood | |
| 4,680,026 A | 7/1987 | Weightman et al. | |
| 4,708,717 A | 11/1987 | Deane et al. | |
| 4,921,478 A | 5/1990 | Solano | |
| 4,957,482 A | 9/1990 | Shiber | |
| 4,964,849 A | 10/1990 | Robicsek | |
| 5,034,000 A | 7/1991 | Freitas et al. | |
| 5,135,492 A | 8/1992 | Melker et al. | |
| 5,203,769 A | 4/1993 | Clement et al. | |
| 5,230,704 A | 7/1993 | Moberg et al. | |
| 5,250,060 A | 10/1993 | Carbo et al. | |
| 5,269,768 A | 12/1993 | Cheung | |
| 5,453,097 A | 9/1995 | Paradis | |
| 5,484,412 A | 1/1996 | Pierpont | |
| 5,496,270 A | 3/1996 | Nettekoven | |
| 5,707,356 A | 1/1998 | Paul | |
| 5,833,650 A | 11/1998 | Imran | |
| 5,902,264 A | 5/1999 | Toso et al. | |
| 5,919,174 A | 7/1999 | Hanson | |
| 6,022,336 A | 2/2000 | Zadno-Azizi et al. | |
| 6,142,980 A | 11/2000 | Schalk | |
| 6,168,577 B1 * | 1/2001 | Niederjohn et al. | 604/23 |
| 6,482,217 B1 * | 11/2002 | Pintor et al. | 606/159 |
| 2002/0052638 A1 * | 5/2002 | Zadno-Azizi | 623/1.2 |

* cited by examiner

Primary Examiner—Sharon Kennedy
(74) Attorney, Agent, or Firm—Kevin J. Boland

(57) ABSTRACT

The present invention is directed to a proximal catheter assembly that is configured to facilitate aspiration through a catheter lumen. The proximal catheter assembly enables natural aspiration to be achieved within the catheter lumen, for example, using an arterial-venous shunt, and further enables suction-assisted aspiration or infusion to be applied through the catheter lumen. This allows a physician to provide a substantially continuous level of retrograde flow within a vessel during a medical procedure without damaging the vessel wall, while providing the option of suction-assisted aspiration, when necessary, to further influence the level of aspiration within the vessel.

18 Claims, 3 Drawing Sheets

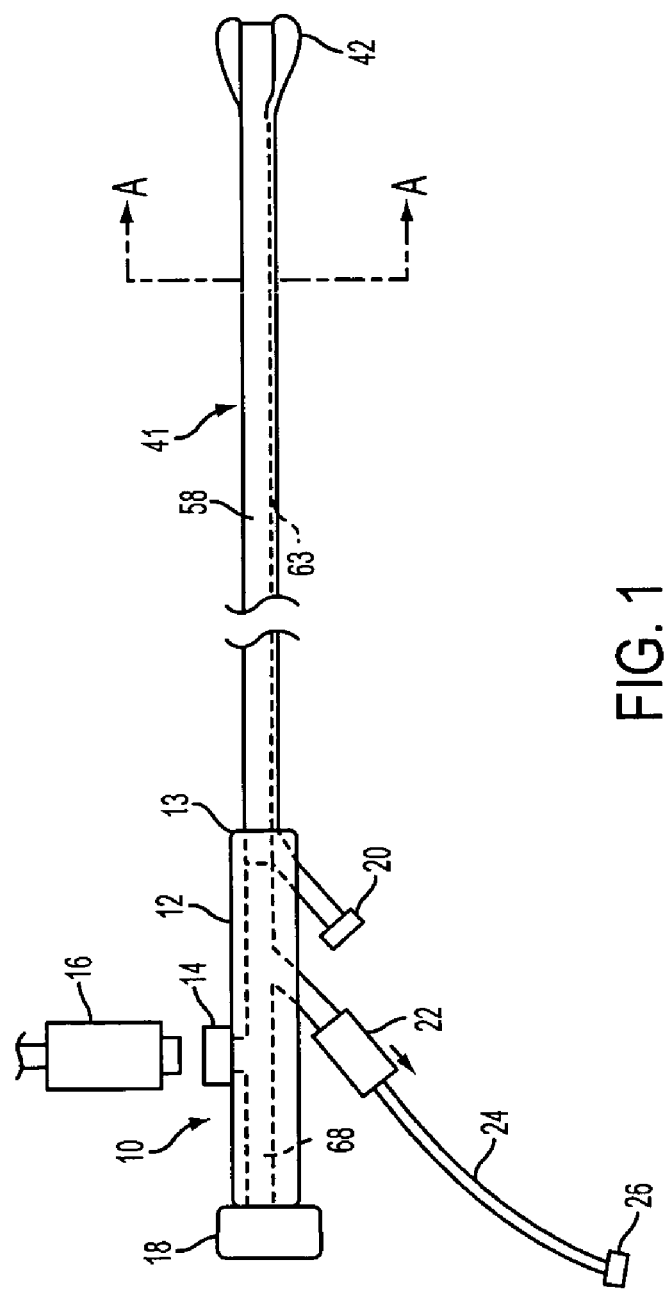
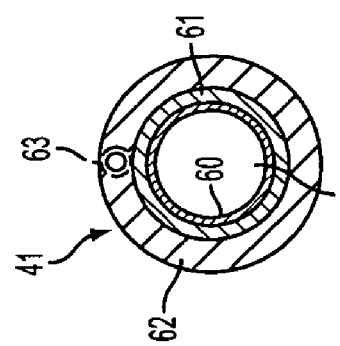
FIG. 1
FIG. 2

PROXIMAL CATHETER ASSEMBLY ALLOWING FOR NATURAL AND SUCTION-ASSISTED ASPIRATION

FIELD OF THE INVENTION

The present invention relates to an improved proximal catheter assembly, and more specifically, a catheter handle that is configured to provide a lumen of a catheter with substantially continuous natural aspiration and, optionally, suction-assisted aspiration.

BACKGROUND OF THE INVENTION

Today there is a growing need to provide controlled access and vessel management during such procedures as stenting, atherectomy or angioplasty. Generally during these procedures there is a high opportunity for the release of embolic material. The emboli may travel downstream from the occlusion, lodging deep within the vascular bed and causing ischemia. The resulting ischemia may pose a serious threat to the health or life of a patient if the blockage forms in a critical area, such as the heart, lungs, or brain.

Several previously known methods and apparatus incorporate the use of an external suction system in conjunction with an aspiration catheter for removal of the clot and/or removal of embolic particles. However, several disadvantages arise when using an external suction system as the sole means for flow management within a vessel. First, it may be difficult to establish the proper aspirating pressure required at the treatment site, and external pressure adjustments used with suction machines may lead to an incorrect amount of suction for a given set of circumstances. If the amount of suction is too low for the circumstances, then embolic particles may not be effectively removed and may travel downstream from the original occlusion, leading to further occlusive events. If the amount of suction is too high, the vessel may collapse.

Moreover, if an external suction device is utilized, retrieval of downstream emboli may require a flow rate that cannot be sustained by the vessel wall for more than a few seconds, resulting in insufficient removal of emboli. Additionally, continuous use of an external suction device may result in excessive blood loss, requiring infusion of non-autologous blood and raising related safety issues.

Other methods for embolic removal have relied on more natural aspirating effects. For example, previous devices have relied on the pressure differential between the atmosphere and blood flow in a treatment vessel to cause a reversal of flow in the treatment vessel. However, such natural aspiration techniques may provide insufficient flow to effectively remove emboli.

In view of these drawbacks of previously know systems, it would be desirable to provide a proximal catheter assembly that allows a catheter to achieve a substantially continuous level of natural, physiologically-regulated aspiration through a working lumen of the catheter.

It also would be desirable to provide a proximal catheter assembly that provides an appropriate level of retrograde flow at a treatment site to direct dislodged particles into a catheter for efficient removal without damaging the treatment vessel.

It further would be desirable to provide a proximal catheter assembly that provides an external suction/infusion port that selectively may be used in conjunction with natural aspiration techniques, to further influence flow in a treatment vessel.

It still further would be desirable to provide a proximal catheter assembly that allows emboli to be filtered and blood reperfused into a patient's vessel to reduce blood loss.

It also would be desirable to provide a proximal catheter assembly that is configured to minimize "back-bleed" that occurs when flow exits through a hemostatic port disposed at the proximal end of a catheter.

SUMMARY OF THE INVENTION

In view of the foregoing, it is an object of the present invention to provide a proximal catheter assembly that allows a catheter to achieve a substantially continuous level of natural, physiologically-regulated aspiration through a working lumen of the catheter.

It is also an object of the present invention to provide a proximal catheter assembly that provides an appropriate level of retrograde flow at a treatment site to direct dislodged particles into a catheter for efficient removal without damaging the treatment vessel.

It is a further object of the present invention to provide a proximal catheter assembly that provides an external suction/infusion port that selectively may be used in conjunction with natural aspiration techniques, to further influence flow in a treatment vessel.

It is yet a further object of the present invention to provide a proximal catheter assembly that allows emboli to be filtered and blood reperfused into a patient's vessel to reduce blood loss.

It is a further object of the present invention to provide a proximal catheter assembly that is configured to minimize "back-bleed" that occurs when flow exits through a hemostatic port disposed at the proximal end of a catheter.

These and other objects of the present invention are accomplished by providing a proximal catheter assembly that is configured to enable two types of aspiration through a catheter lumen. The proximal catheter assembly enables a substantially continuous level of natural, physiologically-regulated aspiration through the catheter lumen using an arterial-venous shunt and, optionally, suction-assisted aspiration through the catheter lumen. This allows a physician to provide a substantially continuous level of retrograde flow in a treatment vessel during a medical procedure, while providing an external suction/infusion port that selectively may be used to further influence the level of aspiration within the vessel. In addition, the suction/infusion port may be used to selectively provide an antegrade flow, e.g., of a therapeutic drug or lytic agent.

In a first embodiment, a proximal catheter assembly of the device of the present invention comprises a handle that is coupled to a catheter, so that a working lumen of the catheter is in fluid communication with a bore of the handle. The handle preferably comprises an external suction/infusion port and at least one hemostatic port, each of which are in fluid communication with the working lumen of the catheter. The handle also is coupled to a blood outlet port that is in fluid communication with the working lumen, and preferably further comprises an inflation port that is in fluid communication with an inflation lumen of the catheter.

In use, the blood outlet port coupled to the handle may be coupled to a venous return line, which is adapted to be disposed in a remote vein. When the venous return line is disposed in the remote vein, and when an occlusive element of the catheter is deployed in a patient's artery, a pressure differential between venous and arterial pressure will cause blood to flow in a retrograde fashion in the artery. Specifically, blood in the artery flows into the working lumen, through the outlet port, and then through the venous return line, where it then is reperfused into the remote vein. A filter may be disposed between the outlet port and the venous return line to remove any emboli prior to reperfusing blood into the remove vein.

This natural, physiologically-regulated aspiration through the outlet port coupled to the catheter handle preferably occurs before, during and after a medical procedure performed through the working lumen of the catheter to effectively remove thrombi and/or emboli from the vessel. Additional suction selectively may be applied by coupling a syringe to the external suction/infusion port, to further influence aspiration of the vessel. Alternatively, the syringe may be used to infuse saline, drugs or other therapeutic agents to the treatment site. The hemostatic port coupled to the handle allows for the delivery of angioplasty, stent delivery systems or other devices to the treatment site.

In an alternative embodiment of the present invention, the proximal catheter assembly further comprises a handle having a roller clamp valve. The roller clamp valve may be used to selectively inhibit flow through the handle, so that "backbleed" from the catheter lumen through the hemostatic port is reduced.

BRIEF DESCRIPTION OF THE DRAWINGS

Further features of the invention, its nature and various advantages will be more apparent from the accompanying drawings and the following detailed description of the preferred embodiments, in which:

FIG. 1 provides a top sectional view of a proximal catheter assembly in accordance with principles of the present invention;

FIG. 2 provides a cross-sectional view along line A—A of FIG. 1;

DETAILED DESCRIPTION OF THE INVENTION

Figure 3A:
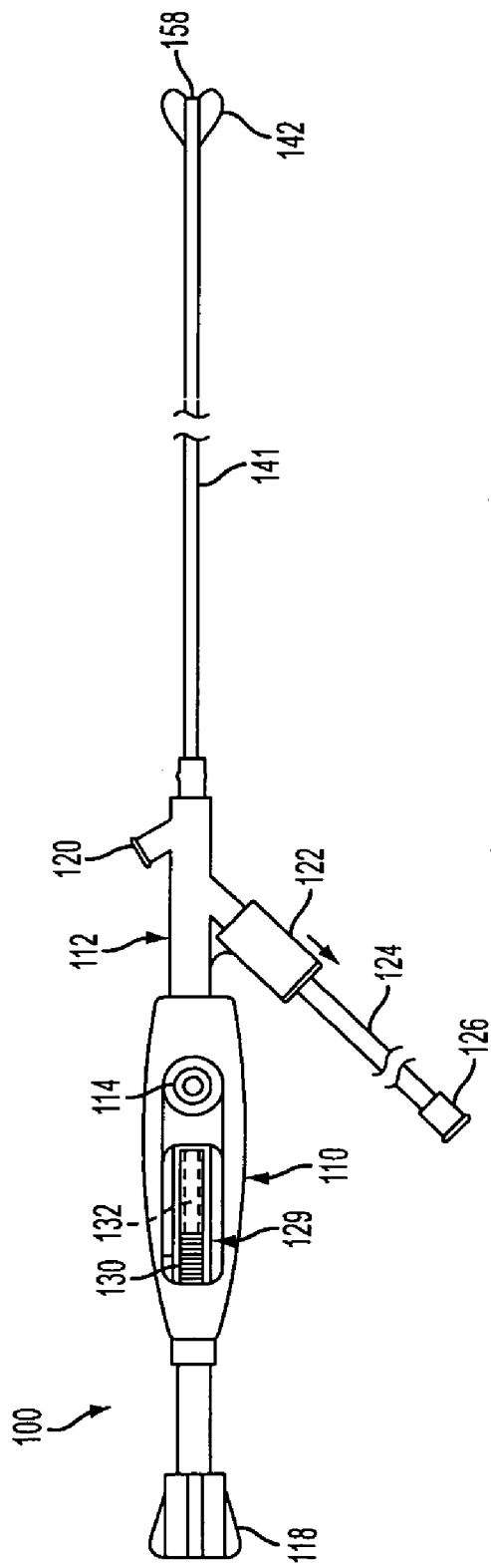
FIGS. 3A–B are, respectively, a top view and a top sectional view of an alternative embodiment of the present invention.

The present invention is directed to a proximal catheter assembly that is configured to enable natural aspiration through a catheter lumen and, optionally, suction-assisted aspiration or infusion through the catheter lumen. The proximal catheter assembly of the present invention enables a substantially continuous level of natural, physiologically-regulated aspiration through the lumen of the catheter by enabling fluid communication between the lumen of the catheter and a patient's venous vasculature. The proximal catheter assembly also provides an external suction/infusion port that may be used in conjunction with a syringe, so that a physician further may influence the level of aspiration through the lumen of the catheter. The provision of substantially continuous retrograde flow and, optionally, selectively increased levels of retrograde flow at a treatment site facilitates removal of emboli during an interventional procedure while minimizing trauma to the treatment vessel. Alternatively, the suction/infusion port may be used to temporarily create antegrade flow in the vessel by introducing a drug or therapeutic agent.

Referring to FIG. 1, a top sectional view of a proximal catheter assembly constructed in accordance with principles of the present invention is described. Proximal catheter assembly 10 is coupled to catheter 41 having proximal and distal ends and working lumen 58 extending therebetween. Proximal catheter assembly 10 comprises handle 12 having proximal and distal ends, and bore 68 extending therebetween. The proximal end of catheter 41 preferably is affixed within bore 68 near distal end 13 of handle 12, so that working lumen 58 of catheter 41 and bore 68 of handle 12 are in fluid communication with each other.

Handle 12 comprises external suction/infusion port 14, which is in fluid communication with bore 68 and working lumen 58 of catheter 41. External suction/infusion port 14 is configured to receive syringe 16, which may be used to induce enhanced aspiration or infusion through working lumen 58.

Handle 12 preferably further comprises inflation port 20, which is in fluid communication with inflation lumen 63 of catheter 41. Inflation lumen 63 further is in fluid communication with occlusive element 42, e.g., a balloon that is disposed at the distal end of catheter 41, so that occlusive element 42 may be deployed via inflation port 20 and inflation lumen 63.

Handle 12 is coupled to blood outlet port 26, which in turn preferably is coupled to a venous return line (not shown) that is adapted to be inserted into a patient's venous vasculature. In a preferred embodiment, one-way check valve 22 is disposed between handle 12 and blood outlet port 26, as shown in FIG. 1, to ensure that flow through the valve occurs exclusively in the direction indicated. For example, when flow is aspirated through catheter 41 via working lumen 58, that flow may enter and pass through one-way check valve 22, then flow through optional tubing 24 and through blood outlet port 26. However, one-way check valve 22 will not allow flow to occur through the valve in an opposite direction, i.e., from blood outlet port 26 into working lumen 58. For example, one-way check valve 22 may close when suction is being provided via syringe 16 to ensure that flow from blood outlet port 26 does not re-enter bore 68 and/or working lumen 58.

Handle 12 of proximal catheter assembly 10 further is coupled to at least one hemostatic port 18, e.g., a Touhy-Borst connector, which is per se known in the art. Hemostatic port 18, bore 68 and working lumen 58 of catheter 41 are sized to permit the advancement of conventional angioplasty catheters, stent delivery systems, thrombectomy systems, and other devices to a vascular treatment site via working lumen 58.

In accordance with principles of the present invention, proximal catheter assembly 10 may be used in conjunction with catheter 41 during a medical procedure to provide a substantially continuous level of natural, physiologically-regulated aspiration through working lumen 58 and, optionally, suction-assisted aspiration.

During the medical procedure, catheter 41 may be disposed in a patient's artery and occlusive element 42 may be deployed. The natural aspiration may be provided through working lumen 58 when a venous return line (not shown), which is coupled to blood outlet port 26, is introduced into a remote vein. Once this arterial-venous circuit is established, negative pressure in the venous line during diastole will establish a low rate continuous flow of blood through working lumen 58 of catheter 41, to the patient's vein via the venous return line. In effect, this arterial-venous shunt allows blood flow in the patient's artery that is distal of occlusive element 42 to flow in a retrograde fashion through working lumen 58, through one-way check valve 22, through outlet port 26, through the venous return line and back into the remote vein. This method, which utilizes the difference between venous and arterial pressure, may be used to provide a substantially continuous level of aspiration at a treatment site before, during and after a medical procedure, to ensure that emboli generated during the medical procedure are directed into working lumen 58 for safe removal. A filter (not shown) may be coupled between blood outlet port 26 and the venous return line so that emboli may be removed and filter blood reperfused into the venous vasculature.

With retrograde flow established in the selected artery via the venous return line, a medical procedure may be performed through hemostatic port 18 and working lumen 58. At any time before, during or after the medical procedure, additional aspiration may be provided at the treatment site via syringe 16. It is preferred that the additional suction provided by syringe 16 only is used in conjunction with the above-described natural aspiration technique for a limited period of time, e.g., at the time a vascular lesion is being traversed or disrupted, to ensure that trauma to the vessel wall due to the external suction is reduced. Alternatively, syringe 16 may be used to temporarily establish antegrade flow, e.g., to infuse contrast agents, drugs, lytic agents or other therapeutic agents.

Referring now to FIG. 2, a cross-section view along section A—A of FIG. 1 is provided. As shown in FIG. 2, catheter 41, which may be used in conjunction with proximal catheter assembly 10, preferably comprises inner layer 60 covered with a layer of flat stainless steel wire braid 61 and polymer cover 62. Inflation lumen 63 is disposed within polymer cover 62 and couples inflation port 20 to occlusive element 42. A proximal end of working lumen 58 is in fluid communication with external suction/infusion port 14, hemostatic port 18, and blood outlet port 26, as described hereinabove with respect to FIG. 1.

Referring now to FIGS. 3, an alternative proximal catheter assembly constructed in accordance with principles of the present invention is described. FIG. 3A provides a top view of proximal catheter assembly 100, which is coupled to catheter 141 having proximal and distal ends and working lumen 158 extending therebetween. Catheter 141 preferably is provided in accordance with catheter 41 of FIGS. 1–2.

Proximal catheter assembly 100 preferably comprises handle 110 and hub 112, each having proximal and distal ends. The distal end of hub 112 is configured to receive and sealingly engage the proximal end of catheter 141, as shown in a top sectional view in FIG. 3B. Working lumen 158 of catheter 141 is in fluid communication with bore 113 of hub 112, which in turn is in fluid communication with lumen 136 of tubing 135, as described in detail with respect to FIGS. 4 hereinbelow.

Proximal catheter assembly 100 further comprises inflation port 120, which preferably is coupled to hub 112 and is in fluid communication with an inflation lumen of catheter 141, e.g., inflation lumen 63 of FIG. 1. The inflation lumen of catheter 141 further is in fluid communication with occlusive element 142 disposed at the distal end of catheter 141, so that occlusive element 142 may be deployed via inflation port 120 and the inflation lumen.

Figure 3B:
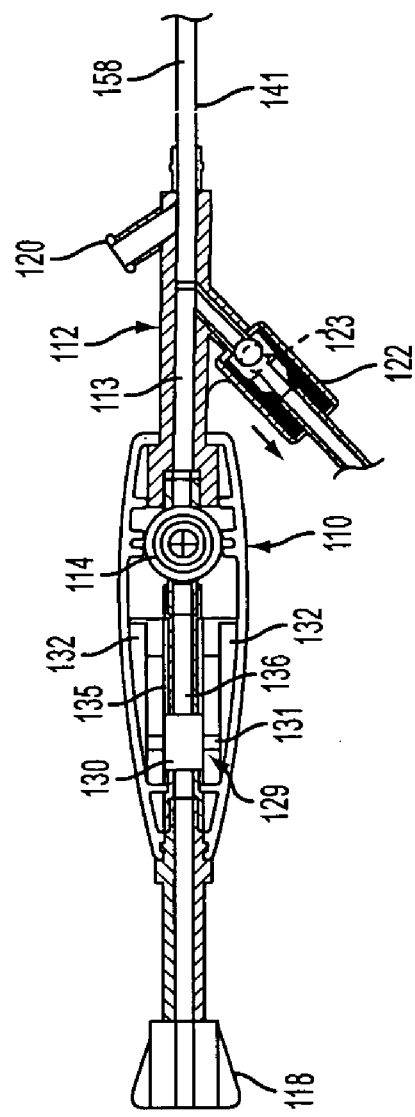
Figure 4A:
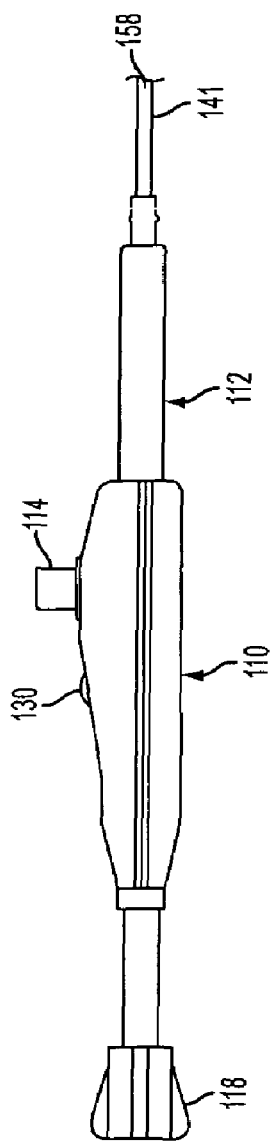
FIGS. 4A–4C are, respectively, a side view and side sectional views of the proximal catheter assembly of FIGS. 3.

Hub 112 of proximal catheter assembly 100 further is coupled to blood outlet port 126, which in turn is coupled to a venous return line (not shown) that is adapted to be inserted into a patient's venous vasculature, as described hereinabove. In a preferred embodiment, one-way check valve 122 is disposed between distal hub 112 and blood outlet port 126 to ensure that flow through one-way check valve 122 occurs only in the direction indicated. As shown in FIG. 3B, one-way check valve 122 preferably comprises ball 123 that is configured to plug an opening of one-way check valve 122, if necessary, to prevent flow from occurring from outlet port 126 into bore 113 and/or working lumen 158.

Figure 4B:
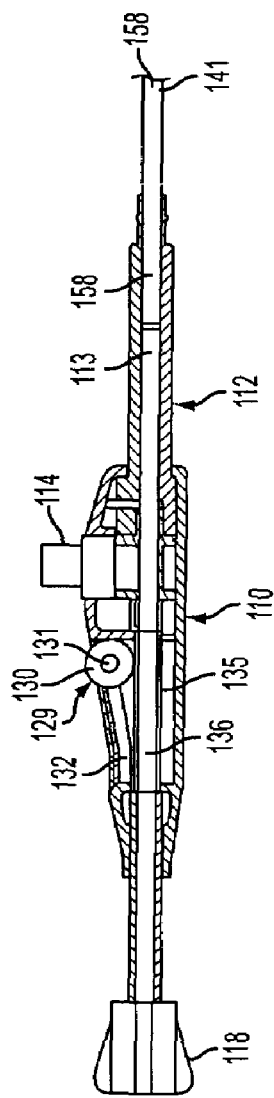
Figure 4C:
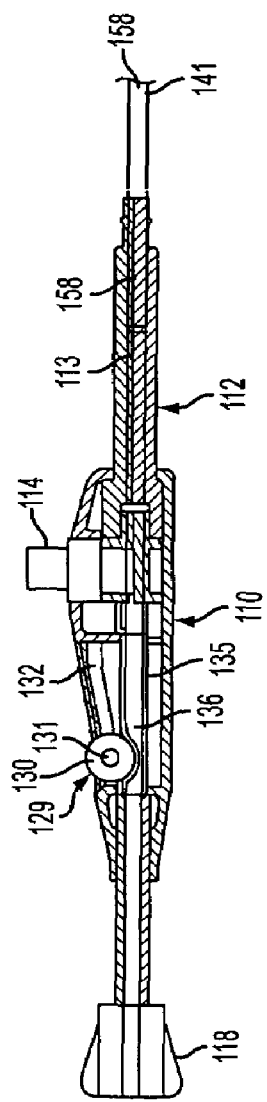

External suction/infusion port 114 preferably is coupled to handle 110 and is in fluid communication with working lumen 158 of catheter 141, as shown in FIGS. 4B–4C. External suction/infusion port 114 is configured to provide external suction through working lumen 158 when a syringe is coupled to port 114. Alternatively, as described hereinabove with respect to port 14 of the embodiment of FIG. 1, port 114 may be used to infuse fluid into the vessel.

Handle 110 further comprises at least one hemostatic port 118 that is in fluid communication with working lumen 158 of catheter 141. Hemostatic port 118 and working lumen 158 are sized to permit the advancement of conventional angioplasty catheters, stent delivery systems, and thrombectomy systems to a vascular treatment site via working lumen 158. As shown in FIG. 3B, and also from side sectional views in FIGS. 4B–4C, handle 110 further comprises a section of tubing 135 that is disposed substantially within handle 110. Tubing 135 comprises lumen 136 that is in fluid communication with hemostatic port 118, external suction/infusion port 114, bore 113 of hub 112 and working lumen 158 of catheter 141.

Handle 110 further comprises roller clamp valve 129, which is configured to selectively inhibit flow through handle 110. Roller clamp valve 129 preferably comprises roller clamp 130 that is mounted on shaft 131, whereby shaft 131 is configured for longitudinal motion within angled slot 132, as shown from a top sectional view in FIG. 3B and from side sectional views in FIGS. 4B–4C. Angled slot 132 is disposed within a portion of handle 110 and tapers from a proximal point in which it is substantially adjacent to tubing 135, as shown in FIG. 4B, to a distal point in which it is further away from tubing 135, as shown in FIG. 4C.

When roller clamp 130 is provided in a distal position within angled slot 132, it will not inhibit fluid transfer occurring within lumen 136 of tubing 135, as shown in FIG. 4B. However, when roller clamp 130 is disposed in a proximal position within angled slot 132, as shown in FIG. 4C, it impinges upon tubing 135 and inhibits flow within lumen 136. In effect, roller clamp valve 129 serves as a switch that allows a physician to selectively inhibit fluid transfer between working lumen 158 of catheter 141 and hemostatic port 118. By inhibiting flow through lumen 136 of tubing 135, roller clamp valve 129 may prevent "backbleed" from occurring when hemostatic port 118 is open, e.g., when catheter 141 is advanced over a guidewire to a treatment site.

In accordance with principles of the present invention, proximal catheter assembly 100 then may be used in conjunction with catheter 141 during a medical procedure to provide a substantially continuous level of natural aspiration and, optionally, syringe-assisted aspiration via external suction/infusion port 114. The preferred method for obtaining the substantially continuous level of natural aspiration using proximal catheter assembly 100 is the same technique described hereinabove with respect to proximal catheter assembly 10 of FIG. 1, which disposes a venous return line in a remote vein and utilizes the difference between venous and arterial pressure to achieve retrograde flow at a treatment site.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. Apparatus suitable for facilitating aspiration through a working lumen of a catheter, the apparatus comprising:
   a handle having proximal and distal ends, and a bore extending therebetween, wherein the handle is coupled to the catheter so that the bore is in fluid communication with the working lumen of the catheter;
   at least one hemostatic port coupled to the apparatus, wherein the hemostatic port is in fluid communication with the working lumen;
   an external port coupled to the handle that is in fluid communication with the working lumen of the catheter;
   a blood outlet port coupled to the handle, wherein the blood outlet port is in fluid communication with the working lumen of the catheter;
   a one-way check valve disposed between the handle and the blood outlet port; and
   wherein the handle enables natural aspiration to be provided through the working lumen via the blood outlet port, and further enables suction-assisted aspiration or infusion to be provided through the working lumen via the external port.

2. The apparatus of claim 1 wherein the one-way check valve causes flow to occur exclusively in a direction from the handle into the blood outlet port.

3. The apparatus of claim 1 wherein the one-way check valve closes to inhibit flow through the one-way check valve when suction is applied via the external port.

4. The apparatus of claim 1 wherein tubing is used to couple the one-way check valve to the blood outlet port.

5. The apparatus of claim 1 wherein the handle further comprises an inflation port that is in fluid communication with an inflation lumen of the catheter.

6. Apparatus suitable for facilitating aspiration through a working lumen of a catheter, the apparatus comprising:
   a hub having proximal and distal ends, and a bore extending therebetween, wherein the hub is coupled to the catheter so that the bore is in fluid communication with the working lumen of the catheter;
   a handle having proximal and distal ends, wherein the distal end of the handle is coupled to the proximal end of the hub;
   at least one hemostatic port coupled to the apparatus that is fluid communication with the working lumen;
   a roller clamp valve disposed within the handle and configured to selectively inhibit fluid communication between the hemostatic port and the working lumen;
   an external port coupled to the handle that is in fluid communication with the bore of the hub and the working lumen of the catheter; and
   a blood outlet port coupled to the hub, wherein the blood outlet port is in fluid communication with the working lumen of the catheter,
   wherein the blood outlet port enables natural aspiration to be provided through the working lumen of the catheter, and the external port enables suction-assisted aspiration or infusion to selectively be provided through the working lumen of the catheter.

7. The apparatus of claim 6 wherein the handle further comprises a section of tubing having a lumen disposed within the handle, wherein the lumen of the tubing is in fluid communication with the hemostatic port and the working lumen.

8. The apparatus of claim 7 wherein the roller clamp valve further comprises:
   a roller clamp mounted on a shaft; and
   an angled slot disposed within the handle, wherein the shaft is configured for longitudinal motion within the angled slot.

9. The apparatus of claim 8 wherein the roller clamp is configured to inhibit flow within the lumen of the tubing by impinging upon the tubing when the shaft is disposed in a first position within the angled slot.

10. The apparatus of claim 9 wherein the roller clamp is configured to permit flow through the lumen of the tubing when the shaft is disposed in a second position within the angled slot.

11. The apparatus of claim 6 further comprising a one-way check valve disposed between the hub and the blood outlet port.

12. The apparatus of claim 11 wherein the one-way check valve causes flow to occur exclusively in a direction from the hub into the blood outlet port.

13. The apparatus of claim 11 wherein the one-way check valve closes to inhibit flow through the one-way check valve when suction is applied via the external port.

14. A method for facilitating aspiration through a working lumen of a catheter, the method comprising:
   providing apparatus comprising a handle having proximal and distal ends, and a bore extending therebetween, wherein the handle is coupled to the catheter so that the bore is in fluid communication with the working lumen of the catheter;
   providing a substantially continuous level of natural aspiration through the working lumen of the catheter using a blood outlet port coupled to the working lumen;
   selectively providing suction-assisted aspiration or infusion through an external port coupled to the handle.

15. The method of claim 14 further comprising advancing a treatment device through the working lumen via a hemostatic port coupled to the apparatus.

16. The method of claim 14 further comprising providing an inflation port coupled to the handle that is in fluid communication with an inflation lumen of the catheter.

17. The method of claim 14 further comprising selectively inhibiting flow through the handle using a roller clamp valve.

18. The method of claim 17 wherein selectively inhibiting flow through the handle using the roller clamp valve comprises causing a roller clamp to impinge upon tubing disposed within the handle.

* * * * *

UNITED STATES PATENT AND TRADEMARK OFFICE
CERTIFICATE OF CORRECTION

PATENT NO. : 6,960,189 B2
DATED : November 1, 2005
INVENTOR(S) : Bates et al.

It is certified that error appears in the above-identified patent and that said Letters Patent is hereby corrected as shown below:

Column 7,
Line 48, after the word "is" insert -- in --.

Column 8,
Line 42, insert -- providing a one-way check valve disposed between the handle and the blood outlet port, wherein the one-way check valve causes flow to occur exclusively in a direction from the working lumen into the blood port; and --.

Signed and Sealed this

Twenty-eighth Day of February, 2006

JON W. DUDAS
*Director of the United States Patent and Trademark Office*